United States Patent [19]

Gardner et al.

[11] 4,417,658
[45] Nov. 29, 1983

[54] SELF-SEALING STERILIZATION BAG

[75] Inventors: Donald E. Gardner, East Islip, N.Y.; David T. Smith, Montville, N.J.

[73] Assignee: Surgicot, Inc., Smithtown, N.Y.

[21] Appl. No.: 360,127

[22] Filed: Mar. 22, 1982

[51] Int. Cl.³ ............................................. B65D 33/20
[52] U.S. Cl. .................................. 206/438; 206/439; 383/66
[58] Field of Search ............... 206/438, 439, 440, 363; 229/62, 80; 150/3

[56] References Cited

U.S. PATENT DOCUMENTS

| 2,878,849 | 3/1959 | Lingenfelter et al. | 150/3 |
| 3,070,280 | 12/1962 | Richmond | 229/80 |
| 3,265,289 | 8/1966 | Hiersteiner | 229/80 |
| 3,326,450 | 6/1967 | Langdon | 229/62 |
| 3,702,171 | 11/1972 | Levine | 229/80 |
| 3,819,106 | 6/1974 | Schuster | 229/80 |
| 4,194,622 | 3/1980 | Lewis | 206/363 |
| 4,276,982 | 7/1981 | Sibrava | 206/439 |
| 4,358,015 | 11/1982 | Hirsch | 229/62 |

Primary Examiner—William T. Dixson, Jr.
Attorney, Agent, or Firm—Lawrence S. Levinson; Donald J. Barrack

[57] ABSTRACT

A sterilizable pouch comprising a plastic web and a paper web marginally heat sealed around all sides thereof, a slit in one of said webs for receiving the package contents and an adhesive strip adhered to the web; said adhesive strip being positioned to cover and seal both lips of the slit, and along with the web to which it is attached forming an assembly which acts as means for opening the slit for insertion of an article.

4 Claims, 4 Drawing Figures

U.S. Patent  Nov. 29, 1983  4,417,658
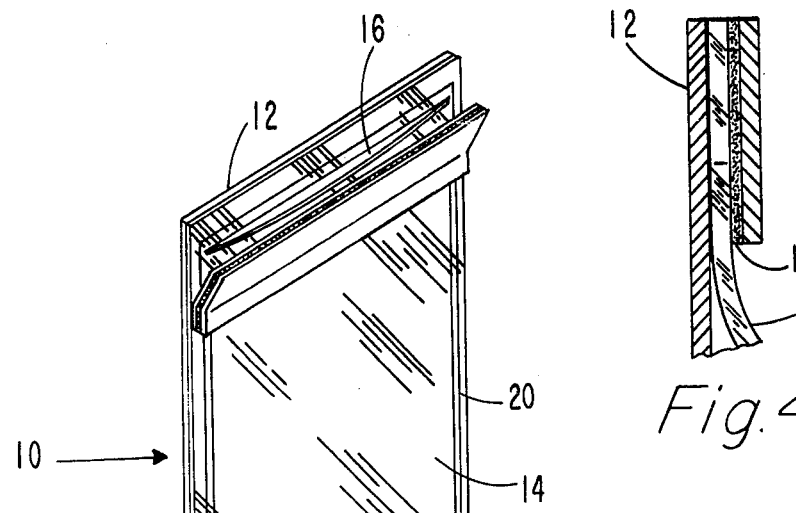
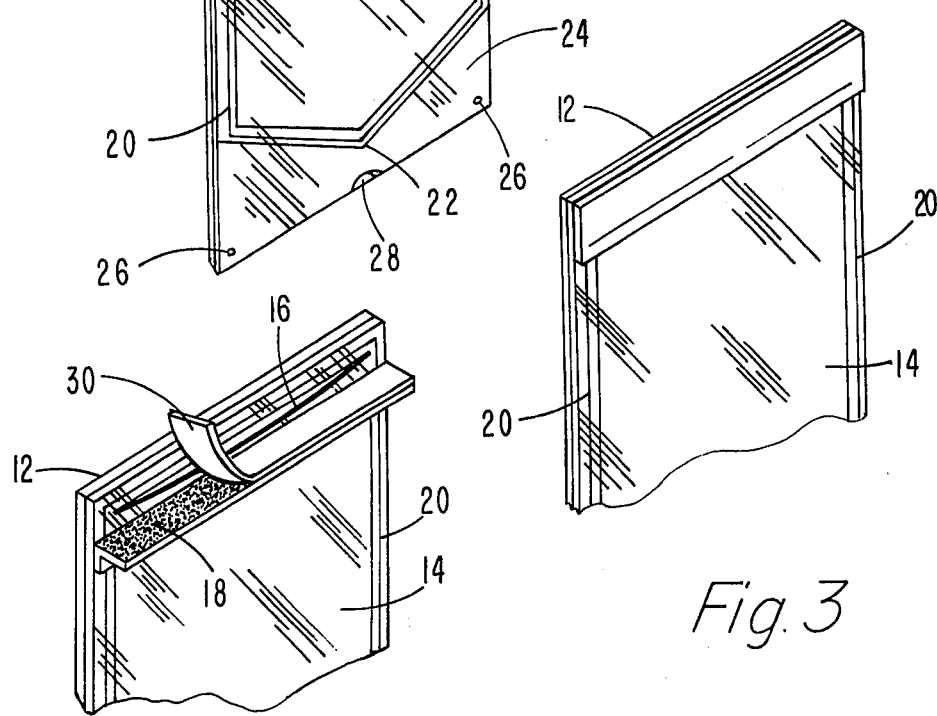

SELF-SEALING STERILIZATION BAG

BACKGROUND OF THE INVENTION

Disposable sterilizable pouches are used in hospitals and other medical facilities to enable the sterilization and storage of instruments, surgeons' gloves and other articles prior to use. They have eliminated the need for sterilization to be carried out immediately preceding use.

In the past, sterilizable pouches have been sealed after insertion of the article, by the use of heat sealing apparatus. More recently, sterilizable pouches have been commercialized which utilize a self-seal concept; i.e., they can be sealed by the user without the benefit of apparatus.

U.S. Pat. No. 3,326,450, issued June 20, 1967, discloses such a package. The package is an open-ended sterilizable envelope formed from a unitary paper blank having an endless cohesive band on one surface thereof.

U.S. Pat. No. 4,276,982, issued July 7, 1981, discloses a sterilizable pouch comprising first and second opposing webs, one of the webs being made from a plastic material and the other being made from a steam permeable paper, and one of the webs having a flap extending outwardly beyond one edge of the other web. This extended flap, in combination with the edge of the other web, defines a mouth for the pouch, the other sides of the pouch being heat sealed. To seal the pouch, a strip of adhesive is present on either of the webs adjacent to and spaced from the mouth, thereby defining an adhesive free zone between the adhesive strip and the mouth of the pouch. The sealing of such a pouch involves a folding operation.

U.S. Pat. No. 4,194,622, issued Mar. 25, 1980, discloses another example of a self-sealing pouch. The pouch comprises plastic and paper webs marginally heat sealed around all of their edges. A slit is provided in the paper member extending between two side seals and adjacent to and spaced from another side seal for receiving the pouch's contents. Adhesive means is disposed on the paper web in such a manner as to provide for the sealing of the slit in response to a single fold around a bending line between the slit and the side seal.

There are also commercially available pouches that are similar to those described in U.S. Pat. No. 4,194,622, but which have the slit in the plastic web.

BRIEF DESCRIPTION OF THE INVENTION

The sterilizable pouch of this invention comprises two webs marginally heat sealed around all sides thereof, a slit in one of said webs for receiving the package contents and an adhesive strip adhered to the web having the slit, said adhesive strip being positioned in such a manner that it will serve as the means for sealing the pouch, and along with the web to which it is attached, will form an assembly which facilitates the locating and opening of the slit for insertion of an article.

BRIEF DESCRIPTION OF THE DRAWINGS

FIG. 1 is an isometric view of an unsealed pouch embodying this invention.

FIG. 2 is an isometric view of a portion of the unsealed pouch of FIG. 1, having the release paper partially removed.

FIG. 3 is an isometric view of a portion of the pouch of FIG. 1 after sealing.

FIG. 4 is a cross-sectional view of the seal portion of FIG. 3.

DETAILED DESCRIPTION OF THE INVENTION

Referring to the drawings which describe a specific embodiment of this invention, the self-sealing sterilizable pouch 10 comprises a paper web 12, a plastic web 14, a slit 16 and an adhesive strip 18.

The pouch 10 is heat sealed 20 around its perimeter. The heat seal 20 should be of sufficient width and strength to withstand the sterilization and mechanical stress conditions to which the pouch 10 will be subjected. As can be seen from the drawings, the heat seal 20 of the embodiment shown is a rib seal; i.e., it is made up of multiple spaced seals. One side of the pouch will preferably be sealed in the shape of a chevron 22, providing an area 24 where the paper 12 and plastic 14 webs are not sealed, to facilitate separating the webs for opening the pouch 10 to remove the sterile article. In a most preferred embodiment, the corners of the unsealed area 24 will have the opposing webs adhesively tacked 26 together to minimize the accumulation of foreign material. Opening of the pouch 10 to remove the sterile article can be further facilitated by inclusion in one of the webs of a thumb cut out 28.

The paper web 12 can be a conventional paper of an artificial paper made from plastic fibers. It is of course essential that the paper be permeable to the sterilant, while impervious to bacteria and dust. Preferably, therefore, the paper will be steam and gas permeable so that one bag can be used for both steam and gas sterilization. The preferred paper for use in this invention is of a kraft construction having an appropriate basis weight.

The plastic web 14 should preferably be made of a material that is transparent, impervious to contaminants, heat sealable and thermally stable. Exemplary plastics are thermoplastic polymers such as polyethylene and polypropylene and polyesters such as polyethylene terephthalate. The plastic web 14 will most preferably be a laminate of a thermoplastic polymer and a polyester, with the polyester being the outer layer.

The slit 16 can be in the paper 12 or plastic 14 web. To prevent tearing of the package, the slit 16 will preferably be in the stronger web. The strength of the webs depends, of course, on the strength of the materials utilized, but the plastic web 14 will usually contain the slit 16. Because of the manner of sealing the slit 16 used by this invention, its location is not at all critical. However, for convenience of usage, the slit 16 will preferably be adjacent to, spaced from, and parallel with, the heat seal on the side of the pouch 10 opposite the chevron 22.

Adjacent to, and spaced from, the slit 16 is an adhesive strip 18 of sufficient size to completely seal the slit 16. The adhesive strip 18, together with the web 14 to which it is attached, forms an assembly which facilitates the locating and opening of the slit 16 for insertion of an article in the pouch 10. The size of the adhesive strip 18 should be sufficient to completely seal the slit 16 by covering both lips of the slit. Preferably, the adhesive strip 18 will extend beyond the edges of the slit 16 to the outer edges of the heat seal 20, thus providing a more contaminant-proof seal.

Preferably the adhesive strip 18 will be a pressure sensitive adhesive, and most preferably a pressure sensitive adhesive with release paper 30 covering that portion of the adhesive not bonding the strip 18 to the web 14. The particular adhesive used is not critical as long as the adhesive is unaffected by sterilization conditions.

The pouch 10 may optionally contain various indicia which are used in the sterilization art; e.g., indicator inks (such as those disclosed in U.S. Pat. No. 3,627,469) which monitor a sterilization process by means of a change in color.

What is claimed is:

1. A sterilizable pouch comprising a plastic web and a paper web marginally heat sealed around all sides thereof, a slit in one of said webs for receiving the package contents and an adhesive strip adhered to the web; said adhesive strip being positioned to cover and seal both lips of the slit, and along with the web to which it is attached forming an assembly which acts as means for opening the slit for insertion of an article.

2. A sterilizable pouch in accordance with claim 1 wherein the slit is in the plastic web.

3. A sterilizable pouch in accordance with claim 1 wherein the seal of one side of the pouch is chevron shaped.

4. A sterilizable pouch in accordance with claim 3 wherein the slit is adjacent to, spaced from and parallel with the heat seal on the side of the pouch opposite the chevron-shaped seal.

* * * * *